United States Patent [19]

Wagner et al.

[11] 4,133,890

[45] Jan. 9, 1979

[54] HYPOLIPIDEMIC COMPOSITIONS AND METHOD EMPLOYING DERIVATIVES OF 4-(((1,3-BENZODIOXOL-5-YL)METHYL)-AMINO)BENZOIC ACID

[75] Inventors: Eugene R. Wagner, Carmel, Ind.; Alfred A. Renzi, Midland; Bobbie J. Allen, Detroit, both of Mich.

[73] Assignee: The Dow Chemical Company, Midland, Mich.

[21] Appl. No.: 818,684

[22] Filed: Jul. 25, 1977

Related U.S. Application Data

[63] Continuation-in-part of Ser. No. 757,119, Jan. 5, 1977, abandoned, which is a continuation-in-part of Ser. No. 650,090, Jan. 19, 1976, abandoned.

[51] Int. Cl.$^2$ .............................................. A61K 31/36
[52] U.S. Cl. .............................. 424/282; 260/340.5 R; 424/310
[58] Field of Search ..................... 424/282, 310, 340.5; 260/518 R, 340.5

[56] References Cited

U.S. PATENT DOCUMENTS

| 3,843,662 | 10/1974 | Holland | 260/293.73 |
| 3,855,255 | 12/1974 | Dohr et al. | 260/410 R |
| 3,868,416 | 2/1975 | Albright et al. | 260/518 R |

OTHER PUBLICATIONS

Chemical Abstracts 38: P2346, 1944.
Chemical Abstracts 58: 521F, Jan. 1963.

*Primary Examiner*—Anna P. Fagelson
*Attorney, Agent, or Firm*—James W. Ambrosius

[57] ABSTRACT

This invention relates to compositions of 4-(((1,3-benzodioxol-5-yl)methyl)amino)benzoic acid the corresponding pharmaceutically-acceptable salts and the esters thereof. The invention also relates to methods for reducing plasma lipid levels in mammals using the compounds and compositions.

15 Claims, No Drawings

HYPOLIPIDEMIC COMPOSITIONS AND METHOD EMPLOYING DERIVATIVES OF 4-(((1,3-BENZODIOXOL-5-YL)METHYL)AMINO)-BENZOIC ACID

CROSS REFERENCE TO RELATED APPLICATION

This application is a continuation-in-part of copending application Ser. No. 757,119 filed Jan. 5, 1977, now abandoned, which is a continuation-in-part of the earlier application Ser. No. 650,090 filed Jan. 19, 1976, now abandoned.

BACKGROUND OF THE INVENTION

As established by various studies, it is recognized that cholesterol and triglycerides play a major role in the formation of artherosclerotic plaques by accelerating the deposition of blood lipids in the arterial wall.

The compound 4-(2-naphthalenylmethyl)amino)benzoic acid has been reported in the literature by Rydon et al. at *J. Chem. Soc.* 1962, pages 4689–4695. The ethyl ester of 4-(((1,3-benzodioxol-5-yl)methyl)amino)benzoic acid is described in German Pat. No. 716,668 (CA38:2346). The free acid is not described and is novel. Neither of the known compounds was reported as useful in lowering serum lipid levels in animals.

Reports in the literature include p-benzylaminobenzoic acid itself. CA51:8720g; 52:18498d; 52:P8539c 55:5867c; 57:14973c. Reported monosubstituted p-benzylaminobenzoic acids include various amino, nitro, and methoxy substitutions. CA65:7001f and CA64:20105g. Several simple multi-substituted analogs have also been reported. CA52:16630b and CA75:141136j. No hypolipidemic activity has been mentioned for any of these compounds. Related compounds are disclosed in U.S. Pat. Nos. 3,257,191; 3,674,843; 3,674,844; 3,780,027 and 3,268,394.

Very few hypolipidemic benzoic acids have been reported until recently. The most important hypolipidemic derivative of benzoic acid disclosed to date is tibric acid. U.S. Pat. No. 3,843,662 and U.S. Pat. No. 3,855,255; see Ryan et al. *Clinc. Pharmacol. Therap.*, 15,218 (1974). There have been two reports of hypolipidemic activity in p-amino benzoic acid analogs. Ger. Offen. No. 2,316,914 (CA82:43070h) and Derwent Abstract BE815-703. A number of patents have issued describing hydroxy and thio benzoic acid derivatives as hypolipidemics or for use in the treatment of heart disease. Japanese Pat. No. 7,333,742 (CA80:133072y); Japanese Pat. No. 7,333,743 (CA80:133073z); German Offen. No. 2,311,020 (CA82:16563g); U.S. Pat. No. 3,716,644; U.S. Pat. No. 3,732,295; Japanese Pat. No. 7,368,541 (CA80:59739c); Derwent Abstract J4 9,070,942; German Offen. No. 1,963,187 (CA75:634-01a); Derwent Abstract 805,172; *Arznei Forsch.*, 22 (2) 465-8 (1972); U.S. Pat. No. 3,856,951; and Derwent Abstract 2,149,070. Alkylamino benzoic acid derivatives have also been described as hypolipidemic agents. U.S. Pat. No. 3,868,416. In addition, there has been much work with compounds having unsaturated bonds for their liquid crystal properties. Derwent Abstract J4 9,052,785 and British Pat. No. 1,373,609.

SUMMARY OF THE INVENTION

The present invention relates to compositions containing 4-(((1,3-benzodioxol-5-yl)methyl)amino)benzoic acid the corresponding pharmaceutically-acceptable salts, amides, and the esters thereof. The invention also relates to a method for reducing plasma lipid levels in animals using the compounds and compositions herein described. The compound 4-(((1,3-benzodioxol-5-yl)methyl)amino)benzoic acid has never been reported in the literature.

The compounds of the present invention are represented by the general formula:

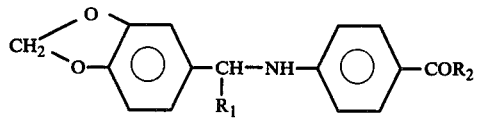

wherein
$R_1$ represents hydrogen or methyl and $R_2$ represents hydroxy, lower alkoxy, amino, N,N-diloweralkylaminoloweralkoxy, and carboxyloweralkylamino. The invention also includes the symmetrical anhydride of the general formula. As used herein the term lower alkyl or lower alkoxy refers to a moiety having from about 1 to 3 carbon atoms.

Pharmaceutically-acceptable salts of the p-aminobenzoic acid, i.e., when R is hydrogen, are considered as being within the scope of this invention. Pharmaceutically-acceptable salts refer to the acid addition salts of those bases which will form a salt with a carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum salts of the instant compound may be obtained by treating the corresponding sodium salt with an appropriate aluminum complex such as aluminum chloride hexahydrate etc.

The compounds employed in the compositions and methods of the present invention are crystalline solids which are soluble in many common organic solvents such as, for example, acetone, benzene, alcohols, and lower alkanes.

Compounds of the present invention have shown hypolipidemic activity in mammals and in particular in primates. Hypolipidemic activity as used herein refers to the effect of lowering the blood lipid content and in particular the cholesterol and triglyceride content of the serum. The compounds of the present invention are therefore suitable for use in treating serum hyperlipidemia in mammals and in particular are useful for the treatment of hypercholesterolemia and hypertriglyceridemia, that is, abnormally high levels of lipids, cholesterol, or triglycerides, respectively, in the serum. The compound 4-(((1,3-benzodioxol-5-yl)methyl)amino)benzoic acid has been found to be particularly active as a hypolipidemic agent in mammals and has the further advantage of showing no significant activity on the central nervous system at those dosages generally used for lowering serum lipids. Relative acute oral toxicity studies conducted in rats for the compound 4-(((1,3-benzodioxol-5-yl)methyl)amino)benzoic acid indicated the median lethal dose ($LD_{50}$) after 7 days was approximately 1.5 grams/kg body weight for males and 2.5 grams/kg body weight for females. The compounds can be administered orally or parenterally by subcutaneous, intravenous, or intraperitoneal injection or by implantation or the like, oral administration being preferred.

The hypolipidemic amount of the p-aminobenzoic acid compounds to be administered to a mammal, that is the amount which is effective to significantly lower the serum lipid level, can vary depending upon such factors as the animal treated, the particular derivative of 4-(((1,3-benzodioxol-5-yl)methyl)amino)benzoic acid employed, the desired lipid level to be obtained whether or not the animal is hyperlipidemic, the period of administration and the method of administration. In general an effective daily dosage range is from about 5 mg/kg of body weight to 400 mg/kg of body weight, with a daily dosage range of from about 10 mg/kg to 100 mg/kg of body weight being preferred.

For oral administration, pharmaceutical preparations of the p-aminobenzoic acid or derivatives thereof may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or cod liver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweetening agents, flowing agents, coloring materials and preservatives.

The p-aminobenzoic acids can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g., at least 1 percent and preferably at least 5 percent, are preferred as they allow for the easier administration of the compound.

DETAILED DESCRIPTION OF THE INVENTION

The active compounds of the present invention are prepared by known procedures. In general, member compounds are made by reacting p-aminobenzoic acid or an ester thereof in an inert solvent with the aldehyde of the organic radical, i.e., piperonal. The resulting Schiff base may be reduced to prepare the corresponding p-aminobenzoic acid derivative. A convenient method of carrying out this latter procedure involves mixing about 0.1 mol. of the Schiff base with an excess of ethanol and water. Dilute aqueous sodium hydroxide, for example about 0.1 molar equivalent of the Schiff base, optionally can be added to the mixture. Sodium borohydride, $NaBH_4$, (0.1 mol.) is added at room temperature and stirred until it dissolves. The mixture is then heated to reflux for 1 to 2 hours. The mixture is poured onto ice and acidified. The product may be filtered off as a precipitate and further purified by known procedures.

The following examples illustrate the preparation of specific compounds of the present invention, but are not to be construed as a limitation thereon.

EXAMPLE 1

Synthesis of 4-(((1,3-benzodioxol-5-yl)methyl)amino)benzoic acid ethyl ester A mixture of 22.5 grams (0.15 mol.) piperonal and 24.8 grams (0.15 mol.) ethyl p-aminobenzoate in 500 ml of benzene was refluxed for several hours until 0.15 mol. of water had been collected in the Dean-Stark trap. The reaction was cooled and yellow crystals formed. The mixture was filtered and the crystalline product was washed with benzene and vacuum dried. This Schiff base weighed 32.0 grams (0.107 mol.).

The Schiff base was dissolved in 500 ml of anhydrous ethanol and warmed to 40° C. Sodium borohydride (4.5 grams) was added as a solid. The resulting slurry was refluxed for 45 minutes. The reaction mass was cooled and poured over 800 ml. of ice water and the crude 4-(((1,3-benzodioxol-5-yl)methyl)amino)benzoic acid ethyl ester precipitated out. The precipitate was collected and washed with water. After vacuum drying 30.4 grams of the white crystalline ester was obtained.

The ester had a melting point of 120–122° C. Elemental analysis showed carbon 68.1%, hydrogen 5.82%, and nitrogen 4.74%. Theoretical analysis of the ester is carbon 68.21%, hydrogen 5.72%, and nitrogen 4.68%.

EXAMPLE 2

Preparation of 4-(((1,3-benzodioxol-5-yl)methyl)amino)benzoic acid

The benzoic acid derivative was prepared from the above ester as follows. A 15 gram portion of the ester was mixed with 150 ml. of 20% sodium hydroxide and 150 ml of ethyl alcohol. The resulting slurry was refluxed for 4 hours and then cooled. The clear solution that resulted was poured onto 800 grams of ice. The reaction mass was acidified with concentrated HCl. Crystalline 4-(((1,3-benzodioxol-5-yl)methyl)amino)-benzoic acid formed and was filtered off, washed with water, and dried. The product was recrystallized from acetonitrile. The compound had a melting point of 193–196° C. Elemental analysis showed carbon 66.7%, hydrogen 4.90% and nitrogen 5.50%. Theoretical analysis of the compound was carbon 66.42%, hydrogen 4.83%, and nitrogen 5.16%.

Alternatively the free benzoic acid derivative can be prepared directly through the reaction of piperonal with p-aminobenzoic acid. The resulting Schiff base can be reduced with sodium borohydride as described above.

EXAMPLE 3

Commercial quantities of 4-(((1,3-benzodioxol-5-yl)methyl)amino)benzoic acid are generally prepared by reacting piperonal with ethyl 4-aminobenzoate in absolute ethanol in the presence of a catalytic amount of 4-toluenesulfonic acid monohydrate to give the intermediate ethyl 4-(((1,3-benzodioxol-5-yl)mehylene)amino)benzoate. The intermediate is isolated and reduced in absolute ethanol using sodium borohydrate. The resulting ethyl 4-(((1,3-benzodioxol-5-yl)methyl)amino)benzoate is not isolated, but immediately hydrolyzed with aqueous sodium hydroxide to give sodium 4-(((1,3-benzodioxol-5-yl)methyl)amino)-benzoate. The salt is converted to 4-(((1,3-benzodioxol-5-yl)methyl)amino)benzoic acid with aqueous acetic acid. The above process has been used to give satisfactory yields and was used to produce a batch containing 33 kg of pharmaceutically-acceptable product.

Using known methods other derivatives of the general formula

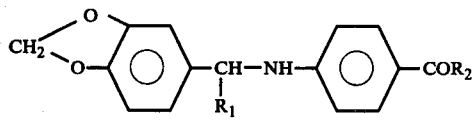

were prepared. These compounds are listed in Table I below.

TABLE I

| Example No. | $R_1$ | $R_2$ |
|---|---|---|
| 4 | H | $-NH_2$ |
| 5 | H | $-O\ominus$. $Na\oplus$ |
| 6 | H | $-O(CH_2)_2N(C_2H_5)_2$ |
| 7 | H | $-O(CH_2)_3N(C_2H_5)_2$ |
| 8 | H | $-NHCH_2COOH$ |
| 9 | $CH_3$ | $-OH$ |

EXAMPLE 10

The hypolipidemic effect of the representative active compounds employed in the practice of the invention is illustratively demonstrated in rats. In this procedure, an active compound as disclosed herein is dissolved in acetone, taken up on a silica gel and mixed with normal ground feed to yield concentrations of 0.125 percent of the compound in the animal feed. The treated feed was administered to male rats weighing 150–160 grams over a 14 day period. Following the 14 day feeding period, the rats were sacrificed, and blood samples were collected. The liver was removed, weighed, and frozen for future analysis. The relative levels of serum cholesterol in the blood samples were determined by the Henly method. A. A. Henly, *Analyst,* 82, 286 (1957). Liver cholesterol was measured by the Sperry-Webb method. *Journal of Biological Chemistry* 187,97 (1950). The relative levels of triglycerides in the blood and liver samples were determined by the Van Handel and Zilversmit method. *J. Lab. Clin. Med.* 50, 152 (1957) and *Clin. Chem.* 7, 249 (1961). Taking the average levels of a similarly treated group of control rats as standard, the mean results obtained in the treated groups is thereby ascertained.

The data presented in Table II summarize the results of the above studies.

TABLE II

| Compound Example Number | Serum Cholesterol* | Serum Triglycerides* | Liver Cholesterol* | Liver Triglycerides* | Liver Weight* |
|---|---|---|---|---|---|
| 1 | −36 | −61 | −2 | 0 | +6 |
| 2 | −32 | −77 | +15 | −21 | +5 |
| 4 | −32 | −70 | +6 | +5 | −4 |
| 5 | −32 | −68 | +10 | −32 | +2 |
| 6 | −28 | −58 | +2 | −23 | +2 |
| 7 | −30 | −66 | +3 | −22 | 0 |
| 8 | −30 | −54 | +8 | −5 | +6 |
| 9 | −40 | −65 | −5 | −36 | +3 |

*all data represent relative change in values for the treated animals when compared to the control group.

The data indicate that the compound 4-(((1,3-benzodioxol-5-yl)methyl)amino)benzoic acid (Example 2) and the various derivatives described herein significantly reduced serum cholesterol and triglycerides while causing only a minimal increase in liver weight.

In addition, the symmetrical anhydride, 4-(((1,3-benzodioxyl-5-yl)methyl)amino)benzoic acid anhydride, was prepared and tested. While somewhat less active than the other derivatives tested this compound reduced serum cholesterol 20% and serum triglycerides 44%.

EXAMPLE 11

The hypolipidemic activity of the sodium salt of 4-(((1,3-benzodioxol-5-yl)methyl)amino)benzoic acid (Example 5) was compared to the free acid (compound Example 2) and the ester (compound Example 1) using the general procedure outlined in Example 10 above. As shown in Table III no significant difference in activity was found between the three compounds as hypolipidemic agents.

TABLE III

| Compound | Serum Cholesterol* | Serum Triglycerides* |
|---|---|---|
| Free Acid (Example 2) | −38 | −75 |
| Ethyl ester (Example 1) | −28 | −60 |
| Sodium salt | −32 | −68 |

*All data represent relative change in values for the treated animals when compared to the control group.

EXAMPLE 12

The hypocholesterolemic effect of 4-(((1,3-benzodioxol-5-yl)methyl)amino)benzoic acid (compound Example 2) was followed in a male and a female cynomalgus monkey (*Macaca fasicularis*). Daily oral doses of 100 mg/kg of body weight with the exception of day seven when 150 mg/kg was given, were administered by nasogastric intubation during the first 2 weeks of the test. The dosage was increased weekly during the last 3 weeks of the test period. The results are shown in Table IV.

TABLE IV

| Test Day | Dosage mg/kg/day | Cholesterol mg/dl male | Cholesterol mg/dl female |
|---|---|---|---|
| −15 | 0 | 199 | 145 |
| −8 | 0 | 170 | 123 |
| 0 | 100 | — | — |
| 7 | 150 | 139 | 103 |
| 8 | 100 | — | — |
| 14 | 150 | 143 | 91 |
| 21 | 200 | 131 | 90 |
| 28 | 300 | 128 | 81 |
| 35 | 400 | 100 | 58 |
| 42 | 500 | 67 | 48 |
| 49 | 500 | 71 | 43 |
| 56 | 500 | 71 | 28 |
| 63 | 500 | 63 | 44 |

The studies indicate that the maximum tolerated dose for the compound of Example 2 was about 500 mg/kg/day in the cynomalgus monkey under the conditions of the test. It should be noted that both monkeys had sustained approximately a 65% reduction in serum cholesterol by day 63.

We claim:

1. A method for lowering serum lipid levels in a mammal which comprises administering internally to the mammal a hypolipidemically effective amount of a compound having the formula

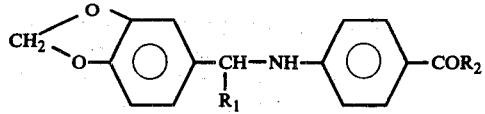

wherein
$R_1$ represents hydrogen or methyl and $R_2$ represents hydroxy, lower alkoxy, amino, N,N-diloweralkylaminoloweralkoxy, or carboxyloweralkylamino; and when $R_2$ is hydroxy, the symmetrical anhydrides or pharmaceutically-acceptable salts of said compound.

2. The method of claim 1 wherein the compound is 4-(((1,3-benzodioxol-5-yl)methyl)amino)benzoic acid.

3. The method of claim 1 wherein $R_2$ is a lower alkoxy of from one to about three carbon atoms.

4. The method of claim 1 wherein the compound is a pharmaceutically-acceptable salt of 4-(((1,3-benzodioxol-5-yl)methyl)amino)benzoic acid.

5. The method of claim 1 wherein $R_2$ is N,N-diloweralkylaminoloweralkoxy.

6. The method of claim 1 wherein $R_2$ is carboxyloweralkylamino.

7. The method of claim 1 wherein the animal is hyperlipidemic.

8. The method of claim 7 wherein the animal is hypercholesterolemic.

9. The method of claim 7 wherein the animal is hypertriglyceridemic.

10. A hypolipidemic composition comprising, a suitable pharmaceutical carrier and a hypolipidemically effective amount of a compound having the formula

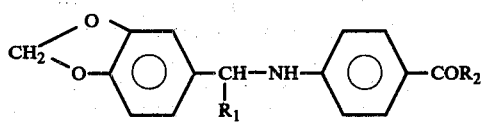

wherein
$R_1$ represents hydrogen or methyl and $R_2$ represents hydroxy, lower alkoxy, amino, N,N-diloweralkylaminoloweralkoxy, or carboxyloweralkylamino; and when $R_2$ is hydroxy, the symmetrical anhydrides or pharmaceutically-acceptable salts of said compound.

11. The composition of claim 10 wherein the compound is 4-(((1,3-benzodioxol-5-yl)methyl)amino)benzoic acid.

12. The composition of claim 10 wherein $R_2$ is a lower alkoxy of from about 1 to 3 carbon atoms.

13. The composition of claim 10 wherein the compound is a pharmaceutically-acceptable salt of 4-(((1,3-benzodioxol-5-yl)methyl)amino)benzoic acid.

14. The composition of claim 10 wherein $R_2$ is N,N-diloweralkylaminoloweralkoxy.

15. The composition of claim 10 wherein $R_2$ is carboxyloweralkylamino.

* * * * *